United States Patent [19]

Friedman

[11] Patent Number: 5,383,463
[45] Date of Patent: Jan. 24, 1995

[54] MAPPING OF FLOW PARAMETERS

[76] Inventor: Zvi Friedman, c/o Elscint Ltd. P.O. Box 550, Haifa 31004, Israel

[21] Appl. No.: 100,163

[22] Filed: Aug. 2, 1993

[51] Int. Cl.$^6$ .................................................. A61B 8/00
[52] U.S. Cl. ................................................... 128/661.09
[58] Field of Search .................. 128/660.04, 660.05, 128/660.07, 660.08, 661.01, 661.08, 661.09

[56] References Cited

U.S. PATENT DOCUMENTS

| | | | |
|---|---|---|---|
| 5,050,611 | 9/1991 | Takamizawa et al. | 128/660.05 |
| 5,090,413 | 2/1992 | Yoshioka | 128/660.05 |

*Primary Examiner*—George Manuel
*Attorney, Agent, or Firm*—Sandler, Greenblum & Bernstein

[57] ABSTRACT

Automatic mapping of flow parameters in a color Doppler ultrasound diagnostic imaging system including the steps of selecting a region of interest (ROI), transmitting ultrasound signals along a plurality of lines traversing the ROI, applying a train of Doppler pulses along each of said lines through blood vessels traversed by said lines during a heart cycle and displaying selected blood flow characteristics in a plurality of colors and preventing misalignment between the sector scan image and the Doppler image by gradually generating both images simultaneously to provide a color flow parameters image superimposed on a two dimensional gray scale image.

9 Claims, 1 Drawing Sheet

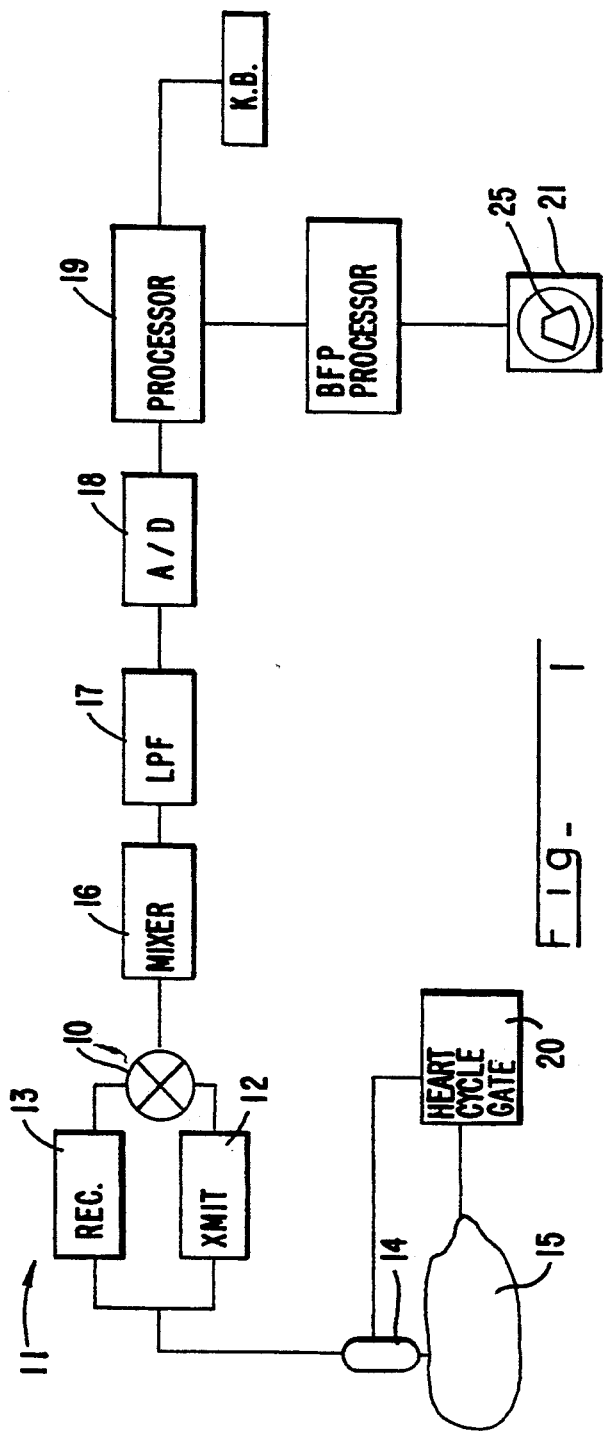
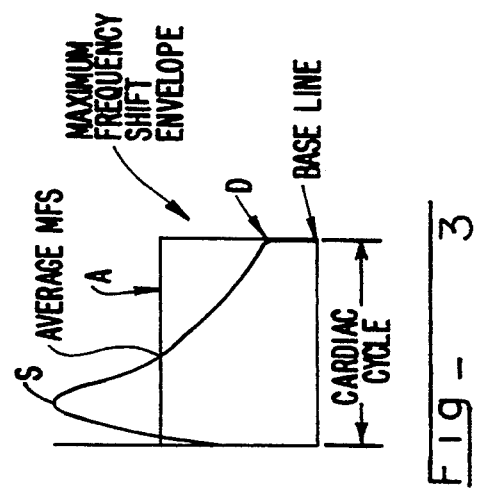
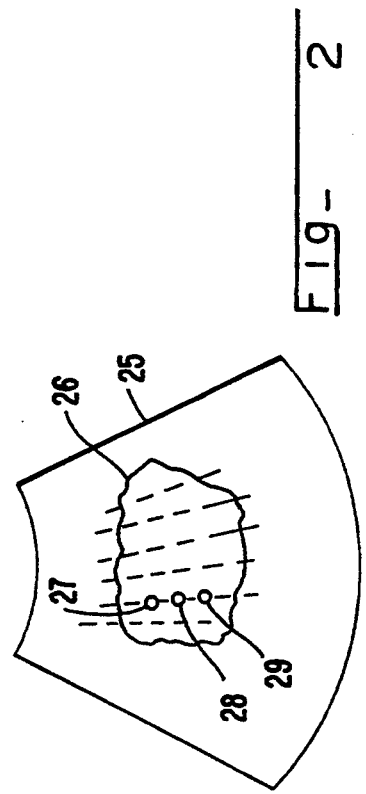

MAPPING OF FLOW PARAMETERS

FIELD OF THE INVENTION

The present invention relates to ultrasonic diagnostic imaging systems and more particularly, to such systems which are capable of displaying a plurality of flow parameters alone or superimposed on an, anatomical image.

BACKGROUND OF THE INVENTION

Diagnostic ultrasound imaging systems provide a comprehensive evaluation of person's health condition. The efficacy of ultrasound techniques have resulted in the widespread acceptance of ultrasound imaging by both patients and physicians. In general, diagnostic ultrasound imaging systems generate images of anatomical structures within the patient by transmitting ultra-high frequency soundwaves (typically in the order of 3.0–10.0 MHz) and then analyzing the waves reflected from the body structure. The most widely used ultrasonic diagnostic systems display structural information of organs in the form of two-dimensional images of selected cross sections of the organ. Typically, the ultrasound is swept across the organ in the form of a sector scan. The sector scan is ordinarily performed in real time so that images are available to the physician during an examination.

In presently available ultrasound systems, in addition to anatomical information, blood flow information is often provided by utilizing the Doppler principle. A beam of ultrasonic energy is directed toward a blood vessel or other organ in which blood flow information is desired. For example, the placenta wherein the blood vessels between the mother and the embryo are interfaced, but not joined. To use the Doppler principle, the beam of ultrasonic energy is directed toward a blood vessel. Moving blood cells reflect the ultrasound energy and either increase or decrease the frequency of the reflected energy depending on the direction of the blood flow in accordance with the well known Doppler principle.

The magnitude of the frequency shift and the direction of the shift are detected so that the direction of the blood flow may be ascertained. Such Doppler ultrasound apparatus also typically provides the usual anatomical information using conventional diagnostic ultrasound techniques.

The Doppler ultrasound equipment now in use, however, fail to provide for mapping of flow parameters other than average velocity of the flow. Thus, while the analysis of blood flow using ultrasound has found a variety of applications in recent years, it has not been used to perform effective mapping of flow parameters other than velocity.

The use of Doppler to study fetal growth is based on the fact that normal fetal growth depends on an adequate supply of oxygen and nutrients which are generally carried to the fetus by the fetal blood through the umbilical placental circulation throughout pregnancy. The studies of the umbilical placental circulation of the human fetus have been greatly facilitated by the use of the aforementioned Doppler ultrasound and analysis of the flow. Recently, there have been some studies wherein the waveforms of the flow velocity have been studied. However, most of these studies have focused on the umbilical artery. The characteristics of the fetal circulation further downstream to the umbilical artery have seldom been studied and certainly, no effective method of using clinical ultrasound has been developed to augment such studies.

Studies of flow parameter characteristics would also be beneficial to determine whether or not a suspicious mass is a malignant tumor. It is known that tumorous masses are generally accompanied by angiogenesis which results in increased diastolic blood flow. This blood flow can be measured and characterized with spectral Doppler. In the past, attempts using spectral Doppler for characterizing tumors have not proved clinically very successful because the neovascularization involves very small blood vessels that are difficult to detect using two-dimensional real time ultrasound imaging, or even using real time color flow imaging, because of its limited sensitivity to slow weak flows.

BRIEF DESCRIPTION OF THE INVENTION

In accordance with a preferred aspect of the present invention, a spectral Doppler ultrasound system that maps blood flow parameters for diagnosing the condition of anatomical organs or carcinomas such as blood flow characteristics in the placenta or in a carcinoma is provided, said system comprising the steps of:

scanning a patient using a gray scale image to detect the mass under study (organ, placenta or carcinoma), analyzing the blood flow into the mass by:

selecting a region of interest;

using spectral Doppler to transmit a plurality of ultrasound beams, selecting plurality of point locations along each of said beams where blood flow through a blood vessel is indicated, applying a train of pulses over a period of time along each of said beams, receiving spectral Doppler echo signals from each of the point locations responsive to said train of pulses, and converting said spectral Doppler signals to blood flow parameters.

The prior art did provide some studies of flow parameters. However, this was accomplished manually using colored Doppler mainly as a guide to detect flow. There were two major deficiencies with the prior art systems. In the first place, it was not able to effectively detect flow parameters in the newly generated small vessels such as are present in the placenta or in malignant tumors. The vessels in such masses are in the order of 50–150 microns, the flow is slow and hard to detect in real time.

It is a feature of the present invention to provide color mapping of flow parameters by using a plurality of parallel point locations along each of the beams for determining the flow parameters at each of the points practically simultaneously whereby the time efficiency of the system makes it clinically effective.

BRIEF DESCRIPTION OF THE DRAWINGS

The above mentioned and other objects and features of the present invention will be best understood when considered in the light of the following description of a preferred embodiment of the present invention wherein:

FIG. 1 is a block diagram showing of an ultrasound Doppler system including the invention.

FIG. 2 is a showing of a sector scan with color flow Doppler point locations, and FIG. 3 is a typical maximum frequency shift envelope.

In FIG. 1, an ultrasound Dopler channel 11 is shown. The two-dimensional channel is not shown as it is well know to those skilled in the art. Channel 11 is shown as comprising a transmitting unit 12 and a receiving unit 13. The transmitting unit comprises the transmitter which transmits pulses of ultrasound waves typically in the order of 3–10 MHz. The waves are transmitted through the transducer 14. The transducer 14 also acts to receive the echoes obtained from the soundwaves when they are reflected by organs in patient 15 in the path of the transmitted soundwaves. Receiver 13 receives these echoes and transmits them to a mixer 16 through switch means 10. The mixer 16 determines the frequency shift of the Doppler signal. A low pass filter 17 then enables the lower frequency signals to pass through to analog digital converter 18 which converts the analog signals into digitized signals which are processed in unit 19 to provide a displayed image 25 in display unit 21.

The displayed image 25 is generally an anatomical image of a sector scan. Along the beams, point locations are placed where the Doppler indicates blood flow; i.e., blood vessels carrying blood. Generally, if the flow is in the direction of the viewer, then the color blue is imaged whereas if it is in the direction away from the viewer, the color red is imaged. Doppler signals are transmitted and received to and from the point locations.

A keyboard or other device 11 is used for inputting user control signals and/or data into the system. The device 22 enables the user to control the process.

Means are provided for synchronizing the transmittal of the Doppler signals with a body function such as, for example, the heart cycle. Such means is indicated in FIG. 1 as heart cycle gate 20. At a selected portion of the heart cycle, the Doppler signal is transmitted at all of the point locations along a beam.

The sector scan obtained by the system of FIG. 1 is shown in FIG. 2 with the organ or mass under study shown at 26. Color portions or point locations indicated at 27, 28 and 29 represent vascular items (veins or arteries) having blood flow. Spectral Doppler is used in the system by first selecting a point or several points; i.e., 27, 28 and 29 that best represent blood flow in the area of tissue under investigation. After the points to be investigated have been selected then automatically a blood flow parameter analysis is made by unit 23 in FIG. 1.

This is done within the blood flow parameter processor 23 after the user determines and inputs the blood flow parameter desired. For example, if the pulsitility index is desired, then the peak diastolic value of the maximum frequency shift envelope S of FIG. 3 is determined. The end diastolic value of the maximum frequency shift envelope D is determined and subtracted from the peak diastolic value of the maximum frequency shift envelope. This difference between the peak diastolic value and end diastolic value is divided by the average value A of maximum frequency shift over the cardiac cycle.

Another parameter that may be of interest is the resistance index. There the same two parameters S and D are subtracted one from the other, but the divisor is the peak systolic value.

The systolic-to-diastolic ratio may be determined which comprises dividing the value S by the value D. Another characteristic of interest is the diastolic average ratio which may be determined by dividing the diastolic value D by the average value of the maximum frequency shift over the cardiac cycle.

Whereas, in the past where the mean flow velocities were displayed in quasi real time at the rate of four to ten frames/sec covering the complete scan sector, it is now proposed to spend the complete heart cycle on each selected line to assure acquiring all data required for mapping the flow parameter. Each of the point locations is subjected to a signal practically simultaneously to provide the flow parameter information in parallel. Further, the inventive method shortens the time required to determine the flow parameters at the specific points by the present method of first determining in a sector scan the location of the blood vessels with the color flow Doppler system and then using the locations as the points at the identified vascular structures. In using the vascular point locations, the time for calculation of blood flow parameters is relatively time-consuming. However, according to the present invention, the use of selected flow index either the RI, PI, SD ratio, or any other index calculable from the above is displayed as a color image superimposed on the two-dimensional image.

Thus, for example, if the resistance index is selected then low resistance index values; i.e., values that are less than 0.4 which are presently accepted as indicating malignancy in a carcinoma mass will be displayed as dark red points and other values will be represented as blue. A typical mode of operation will be that the user preselects a region of interest which the system will then investigate at all points. Since the time required for a full spectrum is in the order of 1–3 sec.; i.e., one to three cardiac cycles, a multigate system which investigates all the points along the scan line or beam in parallel is used.

Conventional color flow imaging systems are multigate systems. In the conventional application of color flow imaging where mean flow velocities are displayed in quasi real time at a rate of 4–10 train of pulses per second, the number of echoes transmitted along one scan line is limited to 4–16 scan lines. The time for a scan line is 1–4 msecs. This time is too short for the calculation of flow parameters. In order to produce the flow index map, the scanning procedure is changed. The scanning is performed line after line with each line scanned for 1–3 secs. Thus, instead of scanning, frame by frame, scanning is done line by line with multiple gates along each line. Scanning is performed line after line with each line scan ranging from 1–3 secs.

A typical region of interest may consist of 50–100 lines and take from 1–3 mins. to scan. The calculation of the flow indices follows in a straight forward manner.

One of the problems that may rise because of the 1–3 mins. acquisition time, which is relatively long, is that of stabilization. The result could be a certain extent of misalignment between the two-dimensional image and the flow index image. That is corrected according to the invention herein by using a TV tracker for tracking on to the two-dimensional image and correlating the original two-dimensional image to the series of two-dimensional images taken during the Doppler scanning in an alternate mode.

Alternatively, the whole region of interest may be scanned as in color flow imaging mode for about 1–3 mins. with the image gradually generated on an evolutionary basis simultaneously throughout the region of interest. The final result will be a color flow parameter image superimposed on the two-dimensional gray scale image. Something not previously obtainable.

Thus, a novel ultrasound diagnostic image system has been disclosed. Although a preferred embodiment of the apparatus has been described in some detail, it is to be understood that various changes could be made by persons skilled in the art without departing from the spirit and scope of the invention as defined by the attached claims.

What is claimed is:

1. A color Doppler ultrasound diagnostic imaging method that provides blood flow parameters for diagnosing a detected mass, said method comprising the steps of:
    selecting a region of interest encompassing said mass;
        transmitting ultrasound signals along a plurality of beams traversing said selected region of interest;
    determining a plurality of point locations to define gated sections along each of said plurality of beams where said beams traverse blood vessels;
    applying a train of Doppler pulses along each of said beams individually during a complete heart cycle, then applying a train of Doppler pulses to a subsequent beam, said pulses to be transmitted to said blood vessels at said point locations to impinge on blood in said blood vessels;
    receiving spectral Doppler signals from said blood in said blood vessels at said point locations; and
    converting said spectral Doppler signals to a selected blood flow parameter.

2. The colored Doppler ultrasound diagnostic imaging method of claim 1 wherein the application of the train of Doppler pulses along each of said beams individually are transmitted to all of said blood vessels traversed by said single beam practically simultaneously during said heart cycle.

3. The color Doppler ultrasound diagnostic imaging method of claim 2 wherein the step of applying a train of Doppler pulses along each of said beams comprises gating said application of the train of pulses to the heart cycle.

4. The color Doppler ultrasound diagnostic imaging method of claim 3 including the step of displaying the selected blood flow parameter in a plurality of colors wherein the first color is used below a certain value of the selected blood flow parameter and a second color is used above that certain value.

5. The color Doppler ultrasound diagnostic imaging method of claim 4 wherein scanning of the sector of the region of interest is performed beam after beam with each beam scan lasting for 1–3 seconds whereby the scan of a typical region of interest may take from 1–3 minutes.

6. The color Doppler ultrasound diagnostic imaging method of claim 5 including the step of preventing misalignment between the sector scan image and the flow parameter image.

7. The color Doppler ultrasound diagnostic imaging method of claim 6 wherein said step of preventing misalignment between the sector scan image and the color blood flow parameter Doppler image comprises locking a TV tracker onto the sector scan image to correlate the original sector scan image to a series of two-dimensional images taken during the Doppler scanning.

8. The color Doppler ultrasound diagnostic imaging method of claim 6 wherein the step of preventing misalignment between the sector scan image and the color blood flow parameter Doppler image comprises gradually generating both the sector scan image and the Doppler image simultaneously throughout the region of interest to provide a color flow parameter image superimposed on the two-dimensional gray scale image.

9. The color Doppler ultrasound diagnostic imaging method of claim 8 wherein the blood flow parameter is a resistance index: that is a systolic peak S of a maximum frequency shift envelope minus the maximum frequency shift envelope value at a diastolic point D divided by the systolic peak S of the maximum frequency shift envelope.
    displaying low resistance index values as dark red points and displaying high resistance index values as blue points where the resistance index values greater than 0.4 are considered high resistance index values.

* * * * *